United States Patent [19]

Beck et al.

[11] Patent Number: 4,634,775

[45] Date of Patent: Jan. 6, 1987

[54] OPTICALLY ACTIVE 3,4-BIS-(DIPHENYLPHOSPHINO)-PYRROLIDINE, AND RHODIUM COMPLEXES, CONTAINING IT AS CHIRAL LIGANDS

[75] Inventors: Wolfgang Beck, Munich; Ulrich Nagel, Weichs, both of Fed. Rep. of Germany

[73] Assignee: Degussa Aktiengesellschaft, Frankfurt am Main, Fed. Rep. of Germany

[21] Appl. No.: 688,360

[22] Filed: Jan. 2, 1985

[30] Foreign Application Priority Data

Jan. 31, 1984 [DE] Fed. Rep. of Germany ....... 3403194

[51] Int. Cl.[4] .......................... C07F 15/00; C07F 9/65
[52] U.S. Cl. .................................... 548/402; 548/412; 548/495; 560/41; 560/40; 560/155; 560/170; 562/444; 562/445; 562/446; 562/450; 562/575
[58] Field of Search .............................. 548/402, 412

[56] References Cited

PUBLICATIONS

Nagel, Angew. Chem., vol. 96, No. 6, pp. 425–426, (1984).
Knowles et al., Advances in Chemistry Series, 196, (1982), American Chemical Society, Washington, D.C., "Catalytic Aspects of Metal Phosphine Complexes", Studies of Asymmetric Homogenous Catalysts, pp. 325–336.
Brunner, Chemie in unserer Zeit, vol. 14, No. 6, pp. 177–183, (1982).
Nagel, Agnew. Chem. Int. Ed. Engl., vol. 23, No. 6, pp. 435–436, (06/84).

Bourson et al., J. Organometallic Chem., vol. 229, pp. 77–84, (1982).
Yatagai et al., Chemistry Letters, No. 8, (1983), pp. 1203–1206.

*Primary Examiner*—Donald G. Daus
*Assistant Examiner*—Diana G. Rivers
*Attorney, Agent, or Firm*—Cushman, Darby & Cushman

[57] ABSTRACT

There are described new optically active 3,4-bis-(diphenylphosphino)-pyrrolidines of the formula

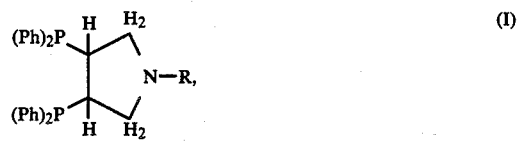

wherein Ph is a phenyl group and R is hydrogen, an alkyl group, an arylalkyl group or an acyl group, rhodium complexes containing a compound of formula (I) as its chiral ligands, said rhodium complexes having the formula

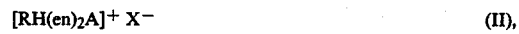

where (en)$_2$ is two molecules of a monoolefin or one molecule of a diolefin, A is an optically active compound of formula (I) and X$^-$ is a tetrafluoroborate, hexafluorophosphate or a perchlorate ion, and use of the rhodium complexes as catalysts for the homogeneous asymmetric hydrogenation of unsubstituted or β-substituted α-acylamino-acrylic acids.

10 Claims, No Drawings

OPTICALLY ACTIVE 3,4-BIS-(DIPHENYLPHOSPHINO)-PYRROLIDINE, AND RHODIUM COMPLEXES, CONTAINING IT AS CHIRAL LIGANDS

BACKGROUND OF THE INVENTION

The invention is directed to new optically active 3,4-bis-(diphenylphosphino)-pyrrolidines, rhodium complexes containing them as chiral ligands and their use as catalysts for the homogeneous asymmetric hydrogenation of unsubstituted or β-substituted α-acylamino-acrylic acids.

There are known from Yatagai, Chemistry Letters (1983) pages 1203 to 1206 optically active pyrrolidine derivatives of the formula

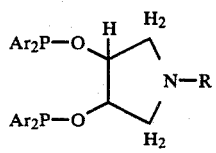

in which Ar is a phenyl group or a methoxyphenyl group and R is an alkyl group or an ω-dimethylaminoalkyl group. These pyrrolidine derivatives can serve as chiral ligands in rhodium complexes, which catalysts are recommended for the asymmetric hydrogenation of dehydrodipeptides. In the asymmetric hydrogenation of α-acetamidocinnamic acid, however, the stereoselectivity of these known rhodium complexes is only slight and consequently also only low optical yields are produced.

SUMMARY OF THE INVENTION

The first subject of the invention are new optically active 3,4-bis-(diphenylphosphino)-pyrrolidines of the general formula

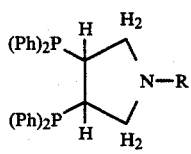

I wherein Ph is a phenyl group and R is hydrogen, an alkyl group, e.g., lower alkyl, an aralkyl group, e.g., phenyl lower alkyl, naphthyl lower alkyl or an acyl group, e.g. from carboxylic acid, e.g., the acyl can have the formula $R_1$—CO— where $R_1$ is hydrogen, lower alkyl, phenyl, napthyl, lower alkoxymethyl, poly(lower alkoxy)methyl of the formula $R_3O(R_4O)_m$—$CH_2$ where $R_3$ and $R_4$ are lower alkyl groups and m is an integer of at least one, or alkoxy.

The base material, namely the 3,4-bis-(diphenylphosphino)-pyrrolidine itself, can be produced by condensing optically active tartaric acid with benzylamine to form 1-benzyl-2,5-dioxo-3,4-dihydroxypyrrolidine, this is reduced by means of lithium aluminum hydride to 1-benzyl-3,4-dihydroxy-pyrrolidine, the benzyl group split off from this by catalytic hydrogenation, the 3,4-dihydroxy-pyrrolidine obtained acylated by means of di-tert.butyl dicarbonate to 1-tert.butoxy carbonyl-3,4-dihydroxy pyrrolidine, this is transformed with methanesulfonic acid anhydride to 1-tert.butoxycarbonyl-3,4-dimethanesulfonylpyrrolidine, this transformed with hydrogen bromide in glacial acetic acid solution into 3,4-dimethethanesulfonylpyrrolidine hydrobromine and finally this reacted with an alkali metal (e.g. sodium) diphenylphosphide to 3,4-bis-(diphenylphosphino)-pyrrolidine, which is isolated as the hydrochloride. If this multi-step synthesis is started with (+)-tartaric acid there is obtained the hydrochloride of (R,R)-3,4-bis-(diphenylphosphino)-pyrrolidine, if the starting material is (−)-tartaric acid, there is formed in corresponding manner the hydrochloride of (S,S)-3,4-bis-(diphenylphosphino)-pyrrolidine. If need be the corresponding free base can then be obtained from the hydrochloride by treatment with an alkali metal hydroxide, hydrogen carbonate or carbonate (e.g. sodium hydroxide, potassium hydroxide, sodium bicarbonate, potassium bicarbonate, sodium carbonate or potassium carbonate).

The free base can subsequently be acylated on the nitrogen atom in known manner with the help of a suitable acylating agent, especially a carboxylic acid chloride or anhydride. Especially preferred acyl derivatives for R in formula (I) are a benzoyl group, a tert-.butoxycarbonyl group or a group of the formula $CH_3$—O—$(CH_2$—$CH_2$—O$)_n$—$CH_2$—CO— where n is an integer from 0 to 3. Examples of additional suitable acyl groups for R are radicals of the formula $R_1$—CO—, where $R_1$ is hydrogen, methyl, ethyl, n-propyl, i-propyl, n-butyl, i-butyl, secondary butyl or tertiary butyl or an α- or β-naphthyl group. These are the preferred acyl groups, but the suitable acyl groups are not limited to these.

The acyl groups can be easily converted in known manner, e.g. by hydrogenation of the carbonyl group by means of lithium aluminum hydride, into the corresponding alkyl or aralkyl group. Especially preferred alkyl or aralkyl groups for R in formula (I) are a methyl, ethyl, or benzyl group. Examples of other suitable alkyl or aralkyl substituents on the pyrrolidine nitrogen atom are n-propyl, i-propyl, n-butyl, i-butyl, n-pentyl, 2 and 3-methylbutyl, 2,2-dimethylpropyl, or a or β-naphthmethyl group. However, other alkyl or aralkyl groups are also suitable.

The thus obtained optically active compounds of formula (I) can serve as chiral ligands in metal complexes which contain rhodium as the central atom.

A further subject of the invention therefore are rhodium complexes of the formula $$[Rh(en)_2A]^+X^- \qquad (II),$$

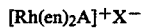

where $(en)_2$ is two molecules of a monoolefin or one molecule of a diolefin, A is an optically active compound of formula (I) and $X^-$ is a tetrafluoroborate, hexafluorophosphate or a perchlorate ion.

Suitable monolefins for the rhodium complex of formula (II) are for example ethylene or cyclooctene (as well as other olefins having 2 to 8 carbon atoms, e.g. propylene, butylene, hexene, cycloheptene, octene). Suitable diolefins for example are 1,3-butadiene, 1,5-cyclooctadiene or norbornadiene (or other diolefins having 4 to 8 carbon atoms). Especially preferred are rhodium complexes of formula II which contain a molecule 1,5-cyclooctadiene.

The rhodium complexes can be produced by reaction of a compound of formula (I) with a rhodium complex of the formula $$[Rh(en)_2Y]_2 \qquad (III),$$

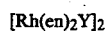

where (en)$_2$ is as defined above and Y is chlorine, bromine, or iodine, with an alkali metal (e.g. sodium or potassium) or silver salt of tetrafluoroboric acid, hexafluorophosphoric acid or perchloric acid.

The rhodium complexes of formula (II) in which (en)$_2$ is a molecule of 1,5-cyclooctadiene and X$^-$ is a tetrafluoroborate anion, can also be produced in an especially simple manner by reacting a compound of formula (I) with a rhodium complex of the formula $$[Rh(COD)_2]^+BF_4 \qquad (IV),$$

where COD stands for 1,5-cyclooctadiene.

A final subject of the invention is the use of the rhodium complexes of formula (II) as catalysts for the asymmetric hydrogenation of unsubstituted or β-substituted α-acylamino-acrylic acids.

As substrates for the asymmetric hydrogenation there can be employed for example α-acylamino-acrylic acids and their derivatives of the general formula

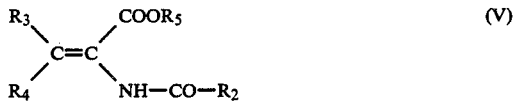

$$\begin{array}{c} R_3 \\ \phantom{R_3} \\ R_4 \end{array} \!\! \diagdown\!\!\! \diagup \!\! \begin{array}{c} \phantom{} \\ C=C \\ \phantom{} \end{array} \!\! \diagdown\!\!\! \diagup \!\! \begin{array}{c} COOR_5 \\ \phantom{} \\ NH-CO-R_2 \end{array} \qquad (V)$$

In this formula R$_5$ is hydrogen, an alkali metal, e.g. soidum or potassium, or a lower alkyl group having 1 to 4, preferably 1 to 2, carbon atoms, e.g. methyl, ethyl propyl, isopropyl, n-butyl, isobutyl, sec.butyl, and R$_2$ is a lower alkyl group having 1 to 4, preferably 1 to 2, carbon atoms, or a phenyl group, R$_3$ and R$_4$ can be the same or different and can be hydrogen, a straight or branched chain alkyl group having 1 to 10 carbon atoms, e.g. methyl, ethyl, propyl, isopropyl, sec.butyl, t-butyl, amyl, hexyl, octyl, decyl, isodecyl, an unsubstituted phenyl or a phenyl substituted in the 3- and/or 4-position by hydroxyl, alkoxy, or acyloxy groups, e.g. 3-hydroxyphenyl, 4-hydroxyphenyl, 3,4-dihydroxyphenyl, 3-methoxyphenyl, 4-methoxyphenyl, 3,4-dimethoxyphenyl, 3-hydroxy-4-methoxyphenyl, 3-acetoxyphenyl, 4-acetoxyphenyl, 3,4-diacetoxyphenyl, 4-propionoxyphenyl, or an indolyl group which is unsubstituted or substituted in the 6-position by a methyl group or by chlorine.

By the asymmetric hydrogenation the prochiral substrates mentioned are converted into the corresponding optically active α-acylaminocarboxylic acids which can be saponified in known manner to the corresponding α-aminocarboxylic acids. If optically active 3,4-bis-(diphenylphosphino)-pyrrolidines of formula (I) originally produced from (+)-tartaric acid are present in the rhodium complex used according to the invention then there are formed in great excess the L-enantiomers of the optically active α-acylaminocarboxylic acids, on the contrary if the starting material is (−)-tartaric acid then there are formed in great excess the D-enantiomers. In both cases, the desired enantiomers can be obtained in optically nearly completely pure form.

The hydrogenation is carried out in customary solvents for hydrogenation such as alcohols, e.g. methanol, ethanol, or isopropanol, and ethers, e.g. dipropyl ether or dioxane, or their mixtures with aliphatic or aromatic hydrocarbons, e.g. hexane, benzene, toluene, or with water. The substrate concentration can range from a 0.001 molar up to a solution supersaturated with substrate. The hydrogen pressure can be between normal pressure and about 80 bar, the reaction temperature between −20° C. and +50° C. Preferably, the hydrogenation is carried out at room temperature. The rhodium complexes containing a compound of formula (I) as chiral ligands are suitably employed in such amounts that the molar ratio of substrate to catalyst is in the range between 1:1 and 50,000:1, preferably between 500:1 to 15,000:1.

Because of the sensitivity of the optically active 3,4-bis-(diphenylphosphino)-pyrrolidines and the rhodium complexes containing them to oxygen, it is suitable to carry out all reactions in a protective gas atmosphere, e.g. under nitrogen or argon and even to store each reaction product under a protective gas. Besides it is recommended to also carry out the hydrogenation under anaerobic conditions.

Unless otherwise indicated all parts and percentages are by weight.

The process can comprise, consist essentially of, or consist of the stated steps with the recited materials. Likewise, the compositions can comprise, consist essentially of, or consist of the stated materials.

The invention will be explained in further detail through the following examples, without limiting the scope of the invention.

DETAILED DESCRIPTION

EXAMPLE 1

(a) Production of 1-Benzoyl-2,5-dioxo-3,4-(R,R)-dihydroxy-pyrrolidine 90 grams (0.6 mole) of L-tartaric acid were treated with 64.2 grams (0.6 mole) of benzylamine and heated to 170° C. with stirring. The reaction water thereby was evaporated. After about 30 minutes the brown liquid became solid and a vacuum was applied for about another 20 minutes. After cooling the still warm crystal paste was digested with ethanol and allowed to stand overnight. The crystals were filtered off with suction, washed with ethanol and recrystallized frm ethanol. Yield: 126 grams, corresponding to 95% of theory. Melting point: 196° to 198° C. (Literature: 196° C.).

(b) Production of 1-Benzyl-3,4-(S,S)-dihydroxy-pyrrolidine 12 grams (0.32 mole) of lithium aluminum hydride were dissolved under nitrogen in 500 ml of diethyl ether (dried over KOH). To the solution there were added at room temperature, all at once, 15 grams (0.068 mole) of the 1-benzyl-2,5-dioxo-3,4-(R,R)-dihydroxy-pyrrolidine produced according to (a). After stirring for 2 days at 35° C. the mixture was cooled to −18° C. and there was slowly dropped in 12 ml of water, whereby hydrogen developed vigorously. Subsequently there were dropped at −10° C. 12 ml of 3.75 molar aqueous sodium hydroxide and finally there were dropped in at 0° C. 25 ml of water. The reaction mixture was allowed to come to room temperature under stirring, the aluminum hydroxide filtered off and extracted with the filtrate in a Soxhlet apparatus. Then the ether was drawn off in a rotary evaporator and the residue taken up in 50 ml of ethyl acetate. The crystals coming out after cooling to −18° C. were filtered off with suction, washed with ethyl acetate/ligroin (1:1 by volume) and dried in a vacuum. Yield: 9.3 grams (71% of theory). Melting point: 100° C.

$[\alpha]_D^{RT} = +32.4°$ (c=4.31, CH$_3$OH).

Elemental analysis: C₁₁H₁₅NO₂ (193.25)

|  | % C | % H | % N |
|---|---|---|---|
| Calculated: | 68.36 | 7.82 | 7.25 |
| Found: | 68.84 | 7.87 | 7.14 |

(c) Production of 3,4-(S,S)-Dihydroxypyrrolidine:

3.86 grams (20 mmoles) of the 1-benzyl-3,4-(S,S)-dihydroxy pyrrolidine produced according to (b) were dissolved in 70 ml of ethanol, treated with 0.5 grams of palladium on activated carbon (10% Pd) and hydrogenated under 1 bar hydrogen pressure. After taking up the theoretical amount of hydrogen, the catalyst was filtered off and the filtrate evaporated to dryness in a vacuum. The residue was sublimed in a high vacuum (bath temperature 100° C., pressure $1.3 \times 10^{-4}$ mbar). Yield: 1.93 grams (94% of theory). Melting point: 101° to 103° C.

$[\alpha]_D^{RT} = +24.9°$ (c=2.13, Ethanol).

Elemental analysis: C₄H₉NO₂ (103.12)

|  | % C | % H | % N |
|---|---|---|---|
| Calculated: | 46.59 | 8.80 | 13.58 |
| Found: | 46.84 | 9.11 | 13.58 |

(d) Production of 1-tert.butoxycarbonyl-3,4-(S,S)-dihydroxy-pyrrolidine:

3.40 grams of the 3,4-(S,S)-dihydroxy-pyrrolidine produced according to (c) were dissolved in 80 ml of ethanol cooled to 0° C. There were added to the solution 10.34 grams (47.4 mmoles) of di-tert.butyl-dicarbonate and the mixture stirred overnight. Then it was heated for 1 hour at 50° C. and finally the solvent drawn off in a vacuum. The residue was heated to boiling in 71 ml of ethyl acetate and 173 ml of toluene and then allowed to cool. After standing at −20° C. for 12 hours the crystals which separated out were filtered off with suction, washed twice with toluene and dried. Yield: 7.30 grams (86% of theory). Melting point: 163° to 165° C.

$[\alpha]_D^{RT} = -21.9°$ (c=3.06, CH₃OH).

Elemental analysis: C₉H₁₇NO₄ (203.24)

|  | % C | % H | % N |
|---|---|---|---|
| Calculated: | 53.19 | 8.43 | 6.89 |
| Found: | 53.49 | 8.31 | 6.85 |

¹H-NMR (CD₃OD)δ(ppm): 4.03, m, 2H (2×CH-OH) 3.20–3.62, m, 4H (2×CH₂) 1.46, s, 9H, (3×CH₃).

(e) Production of 1-tert.Butoxycarbonyl-3,4-(S,S)-dimethanesulfonyl-pyrrolidine:

12.18 grams (59.9 mmoles) of the 1-tert.butoxycarbonyl-3,4-(S,S)-dihydroxy-pyrrolidine produced according to (d) were dissolved in 150 ml of absolute chloroform. The solution was treated with 10.6 ml (131 mmoles) of absolute pyridine and cooled to −50° C. Then there were added all at once, 15 grams (143.5 mmoles) of methanesulfonic acid anhydride and the mixture was immediately cooled to −60° C. The reaction mixture was allowed to slowly come to room temperature and stirred for another 24 hours. The brownish suspension which formed was treated with 300 ml of methylene chloride and shaken three times with an ice cold mixture in each case of 50 ml H₂O and 5 ml of 2N hydrochloric acid. Then the suspension was washed twice, each time with 50 ml of water and dried over MgSO₄. The solvent was drawn off in a vacuum and the residue dried in a high vacuum. Yield: 22.23 grams (100% of theory) of crude product, which still contained traces of chloroform and methylene chloride and was employed without further purification for the next process step.

(f) Production of 3,4-(S,S)-Dimethanesulfonyl-pyrrolidine-hydrobromide 22.03 grams (59.9 mmoles) of the crude 1-tert.butoxycarbonyl-3,4-(S,S)-dimethanesulfonyl-pyrrolidine obtained according to (e) were dissolved with slight warming in 250 ml of ethyl acetate. The slight undissolved portion was filtered off and washed with 50 ml of ethyl acetate. The combined filtrates were cooled to −10° C. and treated with 18 ml of a HBr solution in glacial acetic acid (40% HBr). After 30 seconds a white precipitate began to come out. The reaction mixture was allowed to come to room temperature and then stirred for 24 hours. Then the precipitate was filtered off with suction, washed under nitrogen three times with absolute ether and dried in a high vacuum. Yield: 19.11 grams (94% of theory).

Elemental analysis: C₆H₁₄BrNO₆S₂ (340.22)

|  | % C | % H | % N | % S |
|---|---|---|---|---|
| Calculated: | 21.18 | 4.15 | 4.12 | 18.85 |
| Found: | 21.80 | 4.11 | 4.27 | 18.52 |

(g) Production of 3,4-(R,R)-Bis-(diphenylphosphino)-pyrrolidine-hydrochloride:

10.56 grams (27.5 mmoles) of sodium diphenylphosphide. 2 dioxane was dissolved in 60 ml of absolute dimethyl formamide. The solution was cooled to −35° C. and treated all at once, with 2.6 grams (7.6 mmoles) of the 3,4-(S,S)-dimethanesulfonyl-pyrrolidine-hydrobromide produced according to (f). Then the bath temperature was raised to −12° C. and the mixture stirred for 15 hours. The reaction mixture was allowed to come to room temperature and the solvent was drawn off in a high vacuum at a bath temperature of 20° C. The red residue was treated with 50 ml of degassed water and the aqueous solution extracted once with 55 ml of ether and twice with 15 ml of ether. The combined ether phases were treated with 40 ml of 0.8M hydrochloric acid and stirred vigorously for 15 hours. The precipitated hydrochloride was filtered off, washed with water and ether and dried in a high vacuum at 50° C. Yield: 3.12 grams (80% of theory). Melting point: 184° to 186° C.

$[\alpha]_D^{RT} = +170°$ (c=2.8, Ethanol 99%).

Elemental analysis: C₂₈H₂₈ClNP₂ (475.94)

|  | % C | % H | % N |
|---|---|---|---|
| Calculated: | 70.66 | 5.93 | 2.94 |
| Found: | 70.55 | 6.09 | 2.83 |

³¹p-NMR (CD₃OD/CH₃OH)δ(ppm): −15.28, s.
¹H-NMR (CD₃OD)δ(ppm): 7.6–7.1, m, 20H 4.1–3.6, m, 2H 3.1, m, 4H.

(h) Production of 3,4-(R,R)-Bis-(diphenylphosphino)-pyrrolidine:

0.708 gram (1.49 mmoles) of 3,4-(R,R)-bis-(diphenylphosphino)-pyrrolidine-hydrochloride produced according to (g) were stirred for 1 hour under nitrogen in 20 ml of water which contained 230 mg (4.1 mmoles) of KOH. Then the mixture was extracted three times, each time with 20 ml of ether and the combined ether phases were dried over MgSO₄ and freed from ether in a high vacuum. Yield: 0.644 gram (98.3% of theory).

| Elemental analysis: $C_{28}H_{27}NP_2$ (439.48) | | | |
|---|---|---|---|
| | % C | % H | % N |
| Calculated: | 76.52 | 6.19 | 3.19 |
| Found: | 76.67 | 6.13 | 3.21 |

¹H-NMR (CD₂Cl₂)δ(ppm:): 7.08–7.56, m, 20H (Phenyl), 3.12–3.50 m, 2H (P-C-H̲), 1.83 (broad), 1H (N-H), 2.73–3.00, m, 4H (C-CH₂-N).

$[\alpha]_D^{RT} = +153°$ (c=2.35, Ethanol 99%)

EXAMPLE 2

Production of [(3,4-(R,R)-Bis-(diphenylphosphino)-pyrrolidine)(COD)Rh]BF₄:

574 mg (1.45 mmoles) of [Rh(COD)₂]BF₄ were dissolved in 5 ml of absolute methylene chloride. The solution was cooled to −30° C. and treated with a solution in 20 ml of absolute methylene chloride of 638 mg (1.45 mmoles) of the 3,4-(R,R)-bis-(diphenylphosphino)-pyrrolidine produced according to Example 1(h). After stirring for 5 minutes at −30° C. the cooling bath was removed and after reaching room temperature the mixture was concentrated to about 5 ml in a high vacuum. The rhodium complex precipitated as a yellow powder by the addition of 25 ml of absolute ether. Yield: 1.048 grams (98.03% of theory)

| Elemental analysis: $C_{36}H_{39}NP_2RhBF_4$ (737.37) | | | |
|---|---|---|---|
| | % C | % H | % N |
| Calculated: | 58.64 | 5.33 | 1.89 |
| Found: | 58.67 | 5.51 | 1.86 |

³¹P-NMR (CH₂Cl₂/CH₂Cl₂)δ(ppm): 28.17, d¹$J_{Rh-P}$=148 Hz.

EXAMPLE 3

Hydrogenation With The Rhodium Complex Produced According to Example 2

There were weighed into a 0.5 liter steel autoclave equipped with a magnet lifting stirrer 51.3 grams of α-acetamido-cinnamic acid. The autoclave was closed and evacuated. Then there were sucked into the autoclave 23 mg of the rhodium complex as a solution in 250 ml of absolute methanol. After thorough rinsing with H₂ there were pressed into the autoclave H₂ up to a pressure of 60 bar, the autoclave heated to 50° C. and the stirrer set in motion. After 20 hours the absorption of H₂ was ended and the pressure had fallen to 40 bar. The autoclave was emptied and the methanol drawn off. To remove the catalyst the residue was washed with chloroform and subsequently dried. Conversion: 100%. Yield of N-acetyl-L-phenylalanine: 51.2 grams (98.8% of theory). Melting point: 169° C.

$[\alpha]_D^{RT} = +45.5°$ (c=1, Ethanol 95%), corresponding to a optical yield of 95.8% at reference value $[\alpha]_D^{RT} = +47.5°$.

(b) Analogous to (a) there were hydrogenated in a 0.1 liter steel autoclave 1.04 grams of α-acetamidocinnamic acid in the presence of 6.3 mg of the rhodium-complex Example 3

Solvent: 30 ml Methanol
H₂ beginning pressure: 50 bar
Hydrogenating temperature: room temperature
Hydrogenation time: 15 hours
Conversion: 100%
Optical Yield: 97.5%

EXAMPLE 4

Production of 1-Benzoyl-3,4-(R,R)-bis)-(diphenylphosphino)-pyrrolidine:

559 mg (1.1 mmole) of the 3,4-(R,R)-bis-(diphenylphosphino-pyrrolidine-hydrochloride produced according to Example 1(g) under nitrogen were suspended in 15 ml of water and treated with a solution of 1.5 grams (27 mmoles) of potassium hydroxide in 10 ml of water. The free base was extracted twice, each time with 25 ml of toluene. The combined extracts were dried over magnesium sulfate. After filtration there were added 1 ml (7 mmoles) of triethylamine and subsequently 0.27 ml (2.3 mmoles) of benzoyl chloride. After stirring for one hour there were added 50 ml of water and the phases were separated. The organic phase was washed with 0.5M aqueous sodium hydroxide, water, a 10% aqueous solution of NaH₂PO₄ and finally again with water. The toluene solution was dried over MgSO₄, concentrated to 10 ml and the 1-benzoyl-3,4-(R,R)-bis-(diphenylphosphino)-pyrrolidine precipitated by the addition of n-hexane. The precipitate was filtered off with suction, washed with n-hexane and dried in a high vacuum. Yield 527 mg (89% of theory). Melting point: 180° to 182° C. sealed in the high vacuum).

| Elemental analysis: $C_{35}H_{31}NOP_2$ (543.59) | | | |
|---|---|---|---|
| | % C | % H | % N |
| Calculated: | 77.34 | 5.75 | 2.58 |
| Found: | 77.73 | 5.29 | 2.63 |

$[\alpha]_D^{RT} = +153°$ (c=2.84, Toluene).

EXAMPLE 5

Production of [(1-Benzoyl-3,4-(R,R)-bis-(diphenylphosphino)-pyrrolidine) (COD)Rh]BF₄:

0.20 gram (0.5 mmole) of [Rh(COD)₂]BF₄ and 0.272 grams of the 1-benzoyl-3,4-(R,R)-bis-(diphenylphosphino)-pyrrolidine produced according to Example 4 were stirred for 2 hours in 25 ml of methylene chloride. Then the mixture was concentrated to 2 ml in a vacuum, cooled to −30° C. and there was added a mixture of tetrahydrofuran and diethyl ether (volume ratio 1:2). The yellow precipitate was filtered off with suction at room temperature and washed with ether. Subsequently the rhodium complex was dissolved in methanol and reprecipitated with ether. Yield: 0.38 gram (91% of theory).

| Elemental analysis: $C_{43}NOP_2RhBF_4$ (841.48) | | | |
|---|---|---|---|
| | % C | % H | % N |
| Calculated: | 61.38 | 5.15 | 1.66 |
| Found: | 61.94 | 5.06 | 1.56 |

EXAMPLE 6

Hydrogenation With The Rhodium Complex Produced According to Example 5

The hydrogenation was carried out analogously to Example 3

(a) Reaction vessel: 0.5 liter steel autoclave
Substrate employed: 20.5 grams of α-acetamido-cinnamic acid Amount of rhodium complex employed: 46 mg
Solvent: 200 ml methanol
H₂ beginning pressure: 20 bar
Hydrogenation temperature: 25° to 28° C.
Hydrogenation time: 2 hours
Conversion: 100%
Optical Yield: 97.5%
(b) Reaction vessel: 0.5 liter steel autoclave
Substrate employed: 102.5 grams of α-acetamido-cinnamic acid
Amount of rhodium complex employed: 50 mg
Solvent: 260 ml methanol
H₂ beginning pressure: 55 bar
Hydrogenation temperature: 22° C.
Hydrogenation time: 14 hours
Hydrogen final pressure: 45 bar
Conversion: 100%
Optical Yield: 98.9%
(c) Reaction vessel: 0.1 liter, Erlenmeyer flask equipped with a magnet stirrer and gas inlet
Substrate employed: 1.15 grams of α-acetamido-cinnamic acid
Amount of rhodium complex employed: 29 mg
Solvent: 10 ml methanol
H₂ pressure: 1 bar (from gasometer)
Hydrogenation temperature: 50° C.
Hydrogenation time: 4 hours
Conversion: 100%
Optical Yield: 95.0%
(d) Reaction vessel: 0.1 liter steel autoclave
Substrate employed: 2.05 grams of α-acetamido-cinnamic acid
Amount of rhodium complex employed: 1 mg
Solvent: 30 ml methanol
H₂ beginning pressure: 47 bar
Hydrogenation temperature: room temperature
Hydrogenation time: 19 hours
Conversion: 100%
Optical Yield: 99.0%
(e) Reaction vessel: 0.5 liter steel autoclave
Substrate employed: 3.25 grams of α-acetamido-cinnamic acid
Amount of rhodium complex employed: 1.3 mg
Solvent: 25 ml methanol
H₂ beginning pressure: 60 bar
Hydrogenation temperature: room temperature
Hydrogenation time: 20 hours
Conversion: 98%
Optical Yield: 96.0%
(f) Reaction vessel: 0.1 liter steel autoclave
Substrate employed: 2.1 grams of α-acetamido-cinnamic acid
Amount of rhodium complex employed: 9.9 mg
Solvent: 25 ml methanol saturated with air
H₂ beginning pressure: 47 bar
Hydrogenation temperature: room temperature
Hydrogenation time: 0.5 hours
Conversion: 100%
Optical Yield: 98.0%
(g) Reaction vessel: 0.1 liter Erlenmeyer flask with magnetic stirrer and gas inlet device
Substrate employed: 1.28 grams of α-benzamido-cinnamic acid
Amount of rhodium complex employed: 17.8 mg
Solvent: 15 ml tetrahydrofuran
H₂ pressure: 1 bar (from gasometer)
Hydrogenation temperature: room temperature
Hydrogenation time: 40 hours
Product: N-benzoyl-L-phenylalanine
Conversion: 100%
Optical Yield: 94.4%
(h) Reaction vessel: 0.1 liter steel autoclave
Substrate employed: 1.1 grams of α-acetamido-β-(4-hydroxyphenyl)-acrylic acid
Amount of rhodium complex employed: 5.0 mg
Solvent: 50 ml methanol
H₂ beginning pressure: 65 bar
Hydrogenation temperature: room temperature
Hydrogenation time: 24 hours
Product: N-acetyl-L-tyrosine
Conversion: 100%
Optical Yield: 97.0%
(i) Reaction vessel: 0.1 liter steel autoclave
Substrate employed: B 1.25 grams of α-acetamido-β-(3-methoxy-4-hydroxyphenyl)-acrylic acid
Amount of rhodium complex employed: 5.0 mg
Solvent: 50 ml methanol
H₂ beginning pressure: 65 bar
Hydrogenation temperature: room temperature
Hydrogenation time: 24 hours
Product: N-acetyl-L-(3-methoxy-4-hydroxyphenyl)-alanine
Conversion: 100%
Optical Yield: 100%
(j) Reaction vessel: 0.1 liter steel autoclave
Substrate employed: 1.1 grams of α-acetamido-β-(4-methoxyphenyl)-acrylic acid
Amount of rhodium complex employed: 5.0 mg
Solvent: 50 ml methanol
H₂ beginning pressure: 65 bar
Hydrogenation temperature: room temperature
Hydrogenation time: 15 hours
Product: N-acetyl-L-(4-methoxyphenyl)-alanine
Conversion: 80%
Optical Yield: 100% (corrected to the amount converted)
(k) Reaction vessel: 0.1 liter steel autoclave
Substrate employed: 1.0 g of α-acetamido-β-(3,4-methylenedioxyphenyl)-acrylic acid
Amount of rhodium complex employed: 5.0 mg
Solvent: 50 ml methanol
H₂ beginning pressure: 55 bar
Hydrogenation temperature: room temperature
Hydrogenation time: 15 hours
Product: N-acetyl-L-(3,4-methylenedioxyphenyl)-aeanine
Conversion: 100%
Optical Yield: 93.0%

EXAMPLE 7

Production of 1-tert.Butoxycarbonyl-3,4-(R,R)-bis-(diphenylphosphino)-pyrrolidine 0.78 grams (1.64 mmoles) of the 3,4-(R,R)-bis-(diphenylphoshino)-pyrrolidine-hydrochloride produced according to Example 1(g) was dissolved in 20 ml of chloroform. Then, under nitrogen there was added a solution of 0.23 grams (2.73 mmoles) of sodium bicarbonate and 0.41 grams (7.01 mmoles) of sodium chloride in 20 ml of water. After the ending of the development of gas there was added a solution of 0.40 gram (1.83 mmoles) of di-tert.butyldicarbonate in 10 ml of chloroform and the mixture stirred for 1.5 hours at 50° C. After cooling to room temperature the mixture was stirred for a further 12 hours. Subsequently the organic phase was separated off and the chloroform drawn off. The residue was taken up in 10 ml of diethyl ether and the 1-tert.butoxycarbonyl-3,4-(R,R)-bis-(diphenylphosphino)-pyrrolidine precipitated as a gelatinous white precipitate by addition of mixture of 10 ml of methanol and 5 ml of water. The product was filtered off with suction and dried in a high vacuum.

| Elemental analysis: $C_{33}H_{35}NO_2P_2$ (539.58) | | | |
|---|---|---|---|
| | % C | % H | % N |
| Calculated: | 73.45 | 6.53 | 2.59 |
| Found: | 73.22 | 6.81 | 2.57 |

$^{31}$P-NMR ($CD_2Cl_2/CH_2Cl_2$) δ (ppm): −11.63,s
$^{1}$H-NMR ($d_6$-Aceton) δ (ppm): 7.24–7.55,m,20 H 2.93–4.04, several m, 6 H, all Protons of the ring 1.38, s, 9 H —$CH_3$.
IR: γ($\overline{C=O}$): 1692 cm$^{-1}$.
$[α]_D^{RT}$= +125° (c=3.6, Toluene).

EXAMPLE 8

Production of [1-tert.Butoxycarbonyl-3,4-(R,R)-bis-(diphenylphosphino)-pyrrolidine (COD)Rh]$BF_4$:

There were added to a solution of 249 mg (0.61 mmoles) of [Rh(COD)$_2$]$BF_4$ in 10 ml of absolute methylene chloride at −20° C. 338 mg (0.63 mmoles) of the 1-tert.butoxycarbonyl-3,4-(R,R)-bis-(diphenylphosphino)-pyrrolidine produced according to Example 7 and the reaction mixture was stirred at room temperature overnight. After drawing off the solvent the product was taken up in 5 ml of methanol and the rhodium complex precipitated by the addition of 10 ml of diethyl ether. Yield: 456 mg (89.4% of theory)

| Elemental analysis: $C_{41}H_{47}NO_2P_2RhBF_4$ (837.49) | | | |
|---|---|---|---|
| | % C | % H | % N |
| Calculated: | 58.79 | 5.65 | 1.67 |
| Found: | 58.55 | 5.67 | 1.53 |

$^{31}$P-NMR ($CD_2Cl_2/CH_2Cl_2$) δ (ppm): −33.23, $^{1}J_{Rh-P}$=149.9 Hz.

EXAMPLE 9

Hydrogenation With The Rhodium Complex Produced According To Example 8

The hydrogenation was carried out in a manner analogous to Example 3.

(a) Reaction vessel: 0.5 liter steel autoclave
Substrate employed: 51.3 grams of α-acetamido-cinnamic acid
Amount of rhodium complex employed: 26.2 mg
Solvent: 250 ml methanol
H$_2$ beginning pressure: 60 bar
Hydrogenation temperature: 17° C.
Hydrogenation time: 17 hours
Conversion: 100%
Optical Yield: 97.7%

(b) Reaction vessel: 0.1 liter steel autoclave
Substrate employed: 1.03 grams of α-acetamido-cinnamic acid
Amount of rhodium complex employed: 4.0 mg
Solvent: 25 ml methanol
H$_2$ beginning pressure: 50 bar
Hydrogenation temperature: room temperature
Hydrogenation time: 20 hours
Conversion: 100%
Optical Yield: 99.6%

(c) Reaction vessel: 0.1 liter steel autoclave
Substrate employed: 1.44 grams of α-benzamido-β-(3-indoyl)-acrylic acid
Amount of rhodium complex employed: 3.5 mg
Solvent: 25 ml methanol (substrate present in suspension)
H$_2$ beginning pressure: 50 bar
Hydrogenation temperature: room temperature
Hydrogenation time: 20 hours
Product: N-benzoyl-L-tryptophane
Conversion: 100%
Optical Yield: 81.0%

(d) Reaction vessel: 0.1 liter steel autoclave
Substrate employed: 1.73 grams of α-acetamido-β-(3-methoxy-4-hydroxyphenyl)-acrylic acid
Amount of rhodium complex employed: 5.8 mg
Solvent: 25 ml methanol
H$_2$ beginning pressure: 50 bar
Hydrogenation temperature: room temperature
Hydrogenation time: 20 hours
Product: N-Acetyl-L-(3-methoxy-4-hydroxyphenyl)-alanine
Conversion: 100%
Optical Yield: over 97%

EXAMPLE 10

Production of 1-(β-Methoxyethoxyacetyl)-3,4-(R,R)-bis-(diphenylphosphino)-pyrrolidine:

There was added to a solution of 0.65 gram (1.36 mmoles) of the 3,4-(R,R)-bis-(diphenylphosphino)-pyrrolidine-hydrochloride produced according to Example 1(g) in 20 ml of absolute methylene chloride 0.23 ml (2.8 mmoles) of pyridine. After cooling to −40° C. there was added 0.52 gram (3.4 mmoles) of (β-methoxyethoxy)acetic acid chloride. The reaction mixture was allowed to come to room temperature and stirred for a weekend. Through the addition of diethyl ether the 1-β-methoxyethoxyacetyl)-3,4-(R,R)-bis-(diphenylphosphino)-pyrrolidine precipitated as an oil, which converted into a white powder after stirring for four days in diethyl ether.

The crude product was dissolved in methylene chloride and extracted with 2N HCl. The methylene chloride was drawn off, the residue taken up in ethanol and precipitated with water. The very hygroscopic material was dried for several days in a high vacuum. Yield: 75% of theory.

| Elemental analysis: $C_{33}H_{35}NO_3P_2$, 0.5 $H_2O$ (564.61) | | | |
|---|---|---|---|
| | % C | % H | % N |
| Calculated: | 70.20 | 6.43 | 2.48 |
| Found: | 70.08 | 6.43 | 2.41 |

$^{31}$P-NMR ($CD_2Cl_2$) δ (ppm): −10.17,s.
$^{1}$H-NMR ($CD_2Cl_2$) δ (ppm): 7.13–7.60,m,20H phenyl 3.98,s,2H >N—$COCH_2$—O— 3.31,s,3H, —$OCH_3$, 3.0–4.1, several m, 15 $\overline{H}$ all Protons except phenyl.
$[α]_D^{RT}$= +111±10° (c=2.9, Toluene).

EXAMPLE 11

Production of [(1-(β-Methoxyethoxyacetyl)-3,4-(R,R)-bis-(diphenylphosphino)pyrrolidine)(COD)Rh]$BF_4$:

There were dropped into a solution of 398 mg (0.98 mmoles) of [Rh(COD)$_2$]$BF_4$ in 10 ml of absolute methylene chloride at −30° C. 561 mg (1.00 mmoles) of the 1-(β-methoxyethoxy-acetyl)-3,4-(R,R)-bis(diphenylphosphino)-pyrrolidine produced according to Example 10 as a solution in 10 ml of methylene chloride. After the mixture was stirred overnight at room temperature the methylene chloride ws drawn off in a high vacuum, the residue taken up in 10 ml of methanol and the rhodium complex precipitated by the addition of diethyl ether. After centrifuging the complex was washed with diethyl ether and dried in a high vacuum.

$^{31}$P-NMR (CD$_2$/Cl$_2$) δ (ppm): −35.23,d, $J_{Rh-P}$=149.1 Hz., 35.44,d, $J_{Rh-P}$=149.6 Hz.

$^1$H-NMR (CD$_2$Cl$_2$) δ (ppm): 7.60–8.04,m,Phenyls 5.2 and 4.6, broad, olefinic Protons of COD 3.85, s,>N—CO—CH$_2$—O— 3.41, m, —O—CH$_2$—CH$_2$—O— 3.17, s, —O—CH$_3$ 2.15–3.85, several m, all ring protons and nonolefinic COD-Protons.

EXAMPLE 12

Hydrogenation Of The Rhodium Complex Produced According To Example 4

The hydrogenation was carried out in a manner analogous to Example 3:
(a) Reaction vessel: 0.5 liter steel autoclave
Substrate employed: 51.3 grams of α-acetamido-cinnamic acid
Amount of rhodium complex employed: 26.7 mg
Solvent: 250 ml methanol
H$_2$ beginning pressure: 60 bar
Hydrogenation temperature: 17° C.
Hydrogenation time: 17 hours
H$_2$ final pressure: 40 bar
Conversion: 100%
Optical Yield: 96.8%
(b) Reaction vessel: 0.1 liter steel autoclave
Substrate employed: 1.0 grams of α-acetamido-cinnamic acid
Amount of rhodium complex employed: 4.2 mg
Solvent: 25 ml methanol
H$_2$ beginning pressure: 50 bar
Hydrogenation temperature: room temperature
Hydrogenation time: 20 hours
Conversion: 100%
Optical Yield: 98.7%

EXAMPLE 13

Production of 1-(β-Methoxyethoxyethoxyethoxyacetyl)-3,4-(R,R)-bis-(diphenylphosphino)-pyrrolidine:

There was added to a solution in 20 ml of absolute methylene chloride of 1.04 grams (2.18 mmoles) of the 3,4-(R,R)-bis-(diphenylphosphino)-pyrrolidine-hydrochloride produced according to Example 1(g) 0.35 ml (4.36 mmoles) of pyridine. The solution was cooled to −35° C. and there was added 0.55 gram (2.22 mmoles) of β-methoxyethoxyethoxyethoxy)-acetic acid chloride. After warming to room temperature and stirring overnight the solvent was drawn off, the residue taken up in 10 ml of ethanol and the 1-(β-methoxyethoxyethoxyethoxy-acetyl)-3,4-(R,R)-bis-(diphenylphosphino)-pyrrolidine separated as an oil with pentane. This oil was separated, again treated with pentane, stirred at −40° C. and finally allowed to stand for a week at −25° C. Since no crystallization of the viscous oil took place, the n-pentane was poured off and the residue dried in a high vacuum.

The crude product was dissolved in methylene chloride and extracted with 2N HCl. The methylene chloride was drawn off, the residue taken up in ethanol and precipitated with water. The very hygroscopic material was dried for several days in a high vacuum. Yield: 96% of theory. The product was characterized through $^{31}$P-NMR and $^1$H-NMR.

$^{31}$P-NMR (CH$_2$Cl$_2$) δ (ppm): −10.17.

$^1$H-NMR (CD$_2$Cl$_2$) δ (ppm): 7.10–7.52,m,20H, Phenyls 3.99,s 2H, >N—CO—CH$_2$— 3.59,small, 12 H, —O—CH$_2$—CH$_2$—O— 3.35, s, 3 H —O—CH$_3$ 2.99–4.19,m, all Protons except phenyl.

EXAMPLE 14

Production of [(1-(β-Methoxyethoxyethoxyethoxyacetyl)-3,4-(R,R)-bis-(diphenylphosphino)-pyrrolidine)(COD)Rh]BF$_4$:

There was added to a solution of 362 mg (0.89 mmoles) of [Rh(COD)$_2$]BF$_4$ in 10 ml of methylene chloride at −30° C. a solution of 542 mg (0.84 mmoles) of the 1-(β-methoyethoxyethoxyethoxyacetyl)-3,4-(R,R)-bis-(diphenylphosphino)pyrrolidine produced according to Example 13 in 5 ml of methylene chloride and 5 ml of ethanol and the reaction mixture was stirred at room temperature overnight. Thereby there were formed small amounts of a white precipitate which was filtered off. The rhodium complex was precipitated from the filtrate through the addition of diethyl ether. Yield: 79% of theory. The complex was characterized through $^{31}$P-NMR and $^1$H-NMR:

$^{31}$P-NMR (CD$_2$Cl$_2$) δ (ppm): 33.59, d, $J_{Rh-P}$=149.6 Hz 33.27, d, $J_{Rh-P}$=149.0 Hz.

$^1$H-NMR (CD$_2$Cl$_2$) δ (ppm): 7.43–7.95,m, Phenyls 5.1 and 4.5, broad, olefinic Protons from COD 3.77, s, —CO—CH$_2$ 3.39, m, —CH$_2$—CH$_2$—O— 3.20, s, —O—CH$_3$.

1.68–3.77, several m, all ring protons and non-olefinic COD Protons.

EXAMPLE 15

Hydrogenation With The Rhodium Complex Produced According To Example 14

The hydrogenation was carried out in a manner analogous to Example 3:
(a) Reaction vessel: 0.5 liter steel autoclave
Substrate employed: 51.3 grams of α-acetamido-cinnamic acid
Amount of rhodium complex employed: 29.4 mg
Solvent: 250 ml methanol
H$_2$ beginning pressure: 60 bar
Hydrogenation temperature: 50° C.
Hydrogenation time: 18 hours
H$_2$ final pressure: 40 bar
Conversion: 100%
Optical Yield: 96.4%
(b) Reaction vessel: 0.5 liter steel autoclave
Substrate employed: 51.3 grams of α-acetamido-cinnamic acid
Amount of rhodium complex employed: 14.7 mg
Solvent: 250 ml methanol
H$_2$ beginning pressure: 60 bar
Hydrogenation temperature: 50° C.
Hydrogenation time: 24 hours
H$_2$ final pressure: 40 bar
Conversion: 89%
Optical Yield: 98.4% (corrected to the amount of conversion)
(c) Reaction vessel: 0.1 liter steel autoclave
Substrate employed: 1.0 grams of α-acetamido-cinnamic acid
Amount of rhodium complex employed: 3.4 mg
Solvent: 25 ml methanol
H$_2$ beginning pressure: 50 bar Hydrogenation temperature: room temperature
Hydrogenation time: 20 hours
Conversion: 100%
Optical Yield: 97.6%

EXAMPLE 16

Production of 1-Benzyl-3,4-(R,R)-bis-(diphenylphosphino)-pyrrolidine;

There was dropped into a solution of 1 gram (0.025 mole) of lithium aluminum hydride in 25 ml of a absolute tetrahydrofuran a solution in 25 ml of tetrahydrofuran of 544 mg (1 mmole) of the 1-benzoyl-3,4-(R,R)-bis-(diphenylphosphino)-pyrrolidine produced according to Example 4 and the reaction mixture was stirred overnight. Then there were dropped in 1 ml of water, 1 ml of 3.75 M aqueous sodium hydroxide and finally a further 3 ml of water. The reaction mixture was filtered and the solvent was distilled out of the filtrate in a vacuum. The residue was taken up in toluene and the N-benzyl derivative precipitated through the addition of n-pentane, filtered off with suction and dried. Yield: 0.43 grams (81% of theory).

| Elemental analysis: $C_{35}H_{33}NP_2$ (529.60) | | | |
|---|---|---|---|
| | % C | % H | % N |
| Calculated: | 79.38 | 6.28 | 2.64 |
| Found: | 79.61 | 6.35 | 2.59 |

EXAMPLE 17

Production of [(1-Benzyl-3,4-(R,R)-bis-(diphenylphosphino)-pyrrolidine)(COD)Rh]BF$_4$:

There was stirred for 2 hours a solution of 0.20 gram (0.5 mmole) of [Rh(COD)$_2$]BF$_4$ and 0.265 gram (0.5 mmole) of the 1-benzyl-3,4(R,R)-bis-(diphenylphosphino)-pyrrolidine in 25 ml of methylene chloride. Then it was concentrated in a vacuum to 2 ml and the rhodium complex was precipitated through the addition of diethyl ether, filtered off with suction and dried. Yield: 0.376 gram (91% of theory).

| Elemental analysis: $C_{43}H_{45}NP_2RhBF_4$ (827.5) | | | |
|---|---|---|---|
| | % C | % H | % N |
| Calculated: | 62.41 | 5.48 | 1.69 |
| Found: | 62.38 | 5.55 | 1.68 |

EXAMPLE 18

α-Acetamido-cinnamic acid was hydrogenated with the rhodium complex produced according to Example 17 in a manner analogous to Example 3:

(a) Reaction vessel: 0.1 liter steel autoclave
Substrate employed: 2.05 grams of α-acetamido-cinnamic acid
Amount of rhodium complex employed: 4.1 mg
Solvent: 30 ml methanol
H$_2$ beginning pressure: 47 bar
Hydrogenation temperature: room temperature
Hydrogenation time: 16 hours
Conversion: 100%
Optical Yield: 96.0

The entire disclosure of German priority application P 3403194.4 is hereby incorporated by reference.

What is claimed is:

1. An optically active 3,4-bis-(diphenylphosphino)-pyrrolidine of the formula:

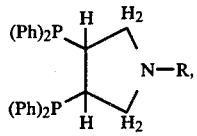

where Ph is a phenyl group and R is hydrogen, an alkyl group, an aralkyl group or an acyl group of the formula R$_1$—CO— where R$_1$ is hydrogen, lower alkyl, phenyl, naphthyl, lower alkoxymethyl, poly(lower alkoxy)methyl of the formula R$_3$O(R$_4$O)$_m$—CH$_2$— where R$_3$ and R$_4$ are lower alkyl groups and m is an integer of at least 1 or alkoxy.

2. A compound according to claim 1 wherein R is hydrogen, lower alkyl, phenyl lower alkyl, naphthyl lower alkyl or acyl of the formula R$_1$—CO—.

3. A compound according to claim 2 wherein R is hydrogen, alkyl of 1 to 5 carbon atoms, benzyl, naphthyl methyl or acyl of the formula R$_1$—CO— where R$_1$ is hydrogen, 1 to 4 carbon atom alkyl, phenyl, naphthyl, CH$_3$—O—(CH$_2$—CH$_2$—O)$_n$—CH$_2$— where n is an integer from 0 to 3, or tert.butoxy.

4. A compound according to claim 3 wherein R methyl, ethyl, benzyl, or acyl of the formula R$_1$—CO— where R$_1$ is phenyl, tert.butoxy, hydrogen, alkyl of 1 to 4 carbon toms, naphthyl or CH$_3$—O—(CH$_2$—CH$_2$—O)$_n$—CH$_2$ where n is an integer from 0 to 3.

5. A rhodium complex of the formula $$[Rh(en)_2A]^+X^- \qquad (II)$$

wherein (en)$_2$ is two molecules of a monoolefin or one molecule of a diolefin, A is an optically active 3,4-bis-(diphenylphosphino)-pyrrolidine of the formula

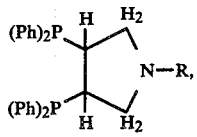

wherein Ph is a phenyl group and R is hydrogen, an alkyl group, an aralkyl group or an acyl group of the formula R$_1$—CO— where R$_1$ is hydrogen, lower alkyl, phenyl, naphthyl, lower alkoxymethyl, poly(lower alkoxy)methyl of the formula R$_3$O(R$_4$O)$_m$—CH$_2$ where R$_3$ and R$_4$ are lower alkyl groups and m is an integer of at least 1 or alkoxy and X$^-$ is a tetrafluoroborate, hexafluorophosphate or a perchlorate anion.

6. A rhodium complex according to claim 5 wherein R is hydrogen, lower alkyl or acyl of the formula R$_1$—CO—.

7. A rhodium complex according to claim 5 wherein R is hydrogen, alkyl of 1 to 5 carbon atoms, benzyl, naphthyl methyl, or acyl of the formula R$_1$—CO— where R$_1$ is hydrogen, 1 to 4 carbon atoms, alkyl, phenyl, naphthyl, CH$_3$—O—(CH$_2$—CH$_2$—O)$_n$—CH$_2$— where n is an integer from 0 to 3, or tert.butoxy.

8. A rhodium complex according to claim 5 wherein R methyl, ethyl, benzyl or acyl of the formula R$_1$—CO— where R$_1$ is phenyl, tert.butoxy, hydrogen, alkyl of 1 to 4 carbon atoms, naphthyl or CH$_3$—O—(CH$_2$—CH$_2$—O)$_n$—CH$_2$— where n is an integer from 0 to 3.

9. A rhodium complex according to claim 5 wherein the monoolefin has 2 to 8 carbon atoms and the diolefin has 4 to 8 carbon atoms.

10. A rhodium complex according to claim 9 wherein the monoolefin is ethylene, propylene, butylene, hexene, cycloheptene, octene or cyclooctene and the diolefin is 1,3-butadiene, 1,5-cycloocatadiene or norbornadiene.

* * * * *